United States Patent [19]

Miyazaki et al.

[11] Patent Number: 5,463,066
[45] Date of Patent: Oct. 31, 1995

[54] PHOSPHOLIPID DERIVATIVE AND REACTIVE VESICLE-FORMING AGENT

[75] Inventors: Tsuyoshi Miyazaki, Tsukuba; Kouzoh Sanchika, Kawasaki; Mitsuhiro Nishida, Amagasaki; Tohru Yasukohchi, Kawasaki; Shigeru Kitano, Tsukuba; Akinori Suginaka, Chigasaki; Yoshihito Kadoma, Kobe, all of Japan

[73] Assignee: NOF Corporation, Tokyo, Japan

[21] Appl. No.: 349,368

[22] Filed: Dec. 5, 1994

[30] Foreign Application Priority Data

Dec. 6, 1993 [JP] Japan .................................. 5-305611
Dec. 6, 1993 [JP] Japan .................................. 5-305612
Dec. 16, 1993 [JP] Japan .................................. 5-317026
Dec. 16, 1993 [JP] Japan .................................. 5-317027

[51] Int. Cl.[6] .............................................. C07D 233/64
[52] U.S. Cl. ...................................................... 548/112
[58] Field of Search ............................................ 548/112

[56] References Cited

U.S. PATENT DOCUMENTS 5,190,822  3/1993  Nishikawa et al. ................ 428/402.2

FOREIGN PATENT DOCUMENTS 0526700   2/1993   European Pat. Off. .
128358    5/1991   Japan .
90/04384  5/1990   WIPO .
91/16040  10/1991  WIPO .
94/22429  10/1994  WIPO .

OTHER PUBLICATIONS

Journal of Liposome Research, vol. 2, No. 3, (5) 1992, New York, pp. 321–334.
Database WPI, Section Ch, Week 9423, Derwent Publications Ltd., London, GB; AN 94–188081 & JP-A-6 126 152 (Nippon Oil & Fats Co. Ltd.), 10 May 1994, Abstract.

*Primary Examiner*—Johann Richter
*Assistant Examiner*—Laura L. Stockton
*Attorney, Agent, or Firm*—Flynn, Thiel, Boutell & Tanis

[57] ABSTRACT

A novel and useful phospholipid derivative to be used for a reactive vesicle-forming agent, which is represented by the following general formula (1):

$$\begin{array}{c} H_2C-OC-R^1 \\ \phantom{H_2C-O}\| \\ \phantom{H_2C-O}O \\ R^2-CO-CH \phantom{-}O \phantom{-}\phantom{-}\phantom{-}\phantom{-}\phantom{-}\phantom{-}\phantom{-}R^3 \\ \phantom{R^2-}\|\phantom{-CO} | \phantom{-}\| \\ \phantom{R^2-}O \phantom{-} H_2C-OP-(X)_p-(OA)_n-O-C-N \\ \phantom{R^2-CO-CH-O-}| \phantom{-(OA)_n-O-}\| \\ \phantom{R^2-CO-CH-O-}OM \phantom{-(OA)_n-O-}O \end{array} \quad (1)$$

in which $R^1C(=O)$ and $R^2C(=O)$ represent each an aliphatic acyl group, $R^3$ denotes hydrogen atom or methyl group, OA represents an oxyalkylene group of 2–4 carbon atoms, n indicates the average addition mole number of added oxyalkylene group and is 1–1,000, p is 0 or 1, X represents $$-OCH_2CH_2N-C(CH_2)_q- \quad \text{or} \quad -OCH_2CH_2N-C(CH_2)_r-C-$$
$$\phantom{-OCH_2CH_2}|\phantom{-}\|\phantom{(CH_2)_q-} \phantom{or\quad -OCH_2CH_2}|\phantom{-}\|\phantom{(CH_2)_r-}\|$$
$$\phantom{-OCH_2CH_2}H\phantom{-}O\phantom{(CH_2)_q-} \phantom{or\quad -OCH_2CH_2}H\phantom{-}O\phantom{(CH_2)_r-}O$$

with q and r being each an integer of 0 to 4 or 1 to 4, respectively, and M denotes hydrogen atom or an alkali metal atom.

4 Claims, No Drawings

PHOSPHOLIPID DERIVATIVE AND REACTIVE VESICLE-FORMING AGENT

FIELD OF THE INVENTION

The present invention relates to a novel and useful phospholipid derivative and to a reactive vesicle-forming agent. More specifically, the present invention relates to a phospholipid derivative and a reactive vesicle-forming agent to be used, for example, for a drug carrier for medicaments etc., testing drugs, diagnostic drugs, sensors, fixed catalysts, bioreactors, bioelectronics elements and a substitute for microcapsules, as well as for the production of various functional vesicles, such as liposome and fat emulsion.

BACKGROUND OF THE INVENTION

Liposome is a lipid vesicle composed of a phospholipid bilayer and has been attempted to find its application in various fields. Attention has been paid, in particular, to the application to drug carrier and sensors for diagnosis and detection, where large problems have been encountered in providing the liposome with a specific function by fixing a special functional substance onto or into the liposome and in maintaining the concentration of such liposome cells in the blood.

Heretofore, there have been reported as for the fixation of functional substances onto or into a liposome, for example, a method in which fragments of an antibody are bound to an aminoethyl carbamoyl-methyl group substituted on the polysaccharide on the surface of a liposome covered with a pullulan derivative via γ-maleimidobutyloxysuccinimidyl [See "Biochem. Biophys. Acta.", 898, 323 (1987)] and a method in which an antibody is fixed onto a liposome in such a manner that a glycolipid is added preliminarily to the ingredients for forming the liposome membrane and, after the liposome has been formed, a periodate oxidation is carried out and the thereby formed aldehyde group is reacted with the antibody [See "J. Biol. Chem.", 255, 10509 (1980)].

These prior arts include, however, a problem that a multistep chemical reaction on the liposome membrane has to be incorporated after the liposome has been formed and, thus, the amount of the contemplated functional substance introduced is limited to a lower value, with simultaneous high possibility of contamination by the by-products and impurities, bringing about a large probability of damage of the liposome membrane.

On the other hand, it has been pointed out that no sufficient effect is achieved by the use of liposome, since a large part of the liposome is caught by organs in the reticuloendothelial system, such as liver, spleen etc., upon administration of the liposome product [Cancer Res., 43, 5328 (1983)]. In order to solve problems by the above-mentioned liposome capture in the organs of reticuloendothelial system and by the low stability of liposome itself, such as the tendency to collapse and coagulation, attempt has been made to introduce polyethylene glycol chains into the surface layer of liposome [See, for example, WO 90/4384, Japanese Patent Application Kokai No. 249717/1989 and FEBS Letters, 268, 235 (1990)]. Also, it has been made clear that a liposome modified by polyethylene glycol can afford to maintain the liposome concentration in blood for long period of time [Biochem. Biophys. Acta, 1066, 29–36 (1991)].

However, the liposome having introduced therein polyethylene glycol chains does not react with functional substances, so that these functional substances can not be fixed on the liposome surface.

In European Patent Publication No. 526700, it is taught that an antibody-bound liposome containing a drug in which the problem of drug capturing in organs of reticuloendothelial system is improved can be obtained by reacting a maleimide group-containing liposome first with a protein provided with thiol groups (thiolated protein) and reacting, then, the remaining maleimide groups with a compound having a moiety of a polyalkylene glycol having thiol groups (thiolated polyalkylene glycol).

This liposome has, however, a defect that the expected effect is not attained sufficiently, since the antibody is hidden behind the polyalkylene glycol layer and the reaction of the antibody with the target site is obstructed.

In WO 91/16040, a liposome preparation is disclosed, which comprises an anionic group-containing polyethylene glycol derivative, such as an α-stearyl-ω-propionic acid-polyoxyethylene. However, this polyoxyethylene derivative tends to separate off easily from the liposome membrane, since the hydrophobic moiety thereof consists of a monoalkyl group, so that a liposome containing such polyoxyethylene derivative as the membrane-forming component is inferior in the long term stability.

SUMMARY OF THE INVENTION

An object of the present invention is to provide a novel and useful phospholipid derivative which permits to fix various functional substances easily and efficiently by a covalent bond onto the top ends of (poly)oxyalkylene chains.

Another object of the present invention is to solve the above-mentioned problems incidental to the prior techniques and to provide a reactive vesicle-forming agent which may be composed of a vesicle, such as a liposome, having provided with (poly)oxyalkylene chains and which permit to fix various functional substances onto the top ends of the (poly)oxyalkylene chains easily and efficiently by a covalent bond and to increase the charged amount of the functional substnce.

The present invention provides, thus, a phospholipid derivative represented by the following general formula (1) and a reactive vesicle-forming agent composed of such phospholipid derivative:

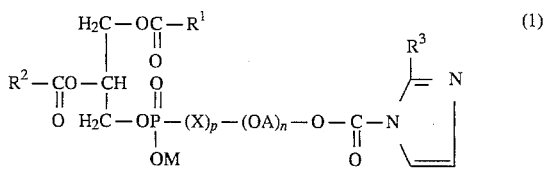

in which $R^1C(=O)$ and $R^2C(=O)$ represent each an aliphatic acyl group having 3–30 carbon atoms and may be identical or different from each other, $R^3$ denotes hydrogen atom or methyl group, OA represents an oxyalkylene group of 2–4 carbon atoms, n indicates the average addition mole number of added oxyalkylene group and is a positive number of 1–1,000, with the proviso that the oxyalkylene groups may be identical or different from each other and may be added randomly or in a block when n is 2 or higher, p is 0 or 1, X represents the group

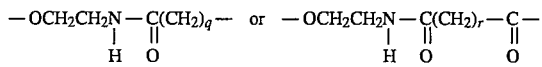

wherein q is an integer of 0 to 4 and r is an integer of 1 to 4 and

M denotes hydrogen atom or an alkali metal atom.

DETAILED DESCRIPTION OF THE INVENTION

In the context of the present application, the term "(poly)oxyalkylene" does mean oxyalkylene or polyoxyalkylene. Similarly, the term "(poly)alkylene" means alkylene or polyalkylene.

The "vesicle" as used in the present invention means a cellular particle having a structure in which the hydrophilic groups of the phospholipid derivative represented by the general formula (1) or of other vesicle-forming components are oriented towards the aqueous phase from the surface membrane. Concrete examples therefor include a closed vesicle composed of a liposome of bimolecular membrane, a fatty emulsion in which a mixture of vegetable oil and phospholipid is emulsified and micells.

The acyl groups of fatty acids represented by $R^1C(=O)$ and $R^2C(=O)$ are those having 3–30, preferably 8–20 carbon atoms inclusive of the carbonyl carbon. Concrete examples of such acyl groups include those of saturated fatty acids, such as propionic acid, butyric acid, caproic acid, caprylic acid, pelargonic acid, capric acid, undecanoic acid, lauric acid, myristic acid, palmitic acid, stearic acid, arachic acid, behenic acid, lignoceric acid, solocic acid, montanic acid, melissic acid, 2-ethyl hexanoic acid; those of unsaturated fatty acids, such as oleic acid, linoleic acid, linolenic acid, erucic acid and 2,4-octadecadienoic acid; those of branched fatty acids, such as isostearic acid; and those of fatty acids having hydroxyl group in the alkyl moiety, such as ricinoleic acid and 12-hydroxy stearic acid.

In the vesicles, such as liposomes and fatty emulsions containing phospholipid derivatives of the general formula (1) as the vesicle-forming component, the acyl groups of fatty acids represented by $R^1C(=O)$ and $R^2C(=O)$ may preferably be those of myristic acid, palmitic acid, stearic acid, oleic acid and 2,4-octadecadienoic acid, in particular, palmitic acid, stearic acid and oleic acid, since these can produce a stable liposome or fatty emulsion. The groups $R^1C(=O)$ and $R^2C(=O)$ may either be identical with or different from each other.

The oxyalkylene group represented by OA in the general formula (1) has 2–4 carbon atoms, namely, for example, oxyethylene, oxypropylene, oxytrimethylene, oxy-1-ethylethylene, oxy-1,2-dimethylethylene and oxytetramethylene. These oxyalkylene groups are derived from addition of alkylene oxides, for example, ethylene oxide, propylene oxide, oxetane, 1-butene oxide, 2-butene oxide and tetrahydrofuran.

The number n in the general formula (1) may be a positive number of 1–1,000, preferably, 10–300 and most preferably 20–120.

In case n is 2 or higher, the oxyalkylene groups in the phospholipid derivative may either be identical with or different from each other. If they are different, they may be in a form of random addition or block addition.

For providing the phospholipid derivative with a hydrophilicity, the group OA may preferably be derived from a sole polyaddition of ethylene oxide, wherein n may preferably be 10 or higher. In case the polyoxyalkylene group is derived from polyaddition of different alkylene oxides, it may preferably be composed of 20 mole % or more, preferably 50 mole % or more of oxyethylene groups. For providing the (poly)oxyalkylene chain with an oleophilicity, the number of moles of added alkylene oxide other than ethylene oxide is increased.

In the general formula (1), p denotes 0 or 1 and, if p=1, x is selected from the bivalent organic groups mentioned above.

$R^3$ of the general formula (1) represents a hydrogen atom or a methyl group and M denotes hydrogen atom or an alkali metal atom, such as sodium or potassium.

In case p of the general formula (1) is 1, the phospholipid derivative is represented by the general formula (1-1) or (1-2) given below and, if p is zero, it is represented by the general formula (1-3) also given below:

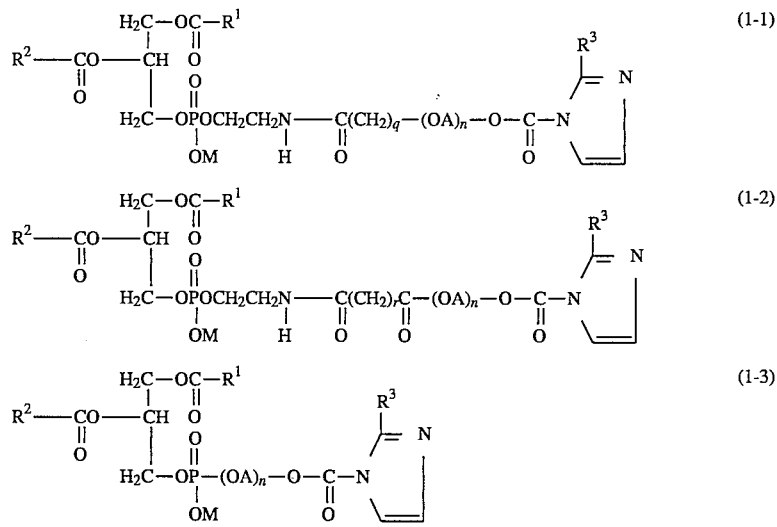

In these general formulae, the symbols same with those of general formula (1) have the same meanings.

The phospholipid derivative of general formula (1-1), namely that of general formula (1) with P=1, can be produced easily by, for example, reacting a (poly)oxyalkylene derivative having a carboxyl group at its one end and a hydroxyl group at the other end with N,N'-dicyclohexylcarbodiimide (DCC) to form an active derivative and subjecting this derivative then to a reaction with a phosphatidylethanolamine, whereupon the resulting product is reacted with N,N'-carbonyldiimidazole (CDI). The production procedures using an α-hydro-ω-carboxyl polyoxyethylene [α-(2-carboxy)ethyl-ω-hydroxy polyoxyethylene] for the (poly)oxyalkylene derivative and dipalmitoyl-glycero-phosphoethanolamine (DPPEA) for the phosphatidylethanolamine is given in the following reaction scheme (2a):

ends each an oxycarbonyl imidazole group in a mixing mole proportion of 1:1 to 1:1,000. By this, phospholipid derivatives of the general formula (1-1) with q=0 are obtained.

The above reactions can be realized without solvent or in an aqueous medium, such as water, saline, a phosphate buffer, a tris buffer, a carbonate buffer or a borate buffer, or further in an organic solvent, such as toluene, acetonitrile, methanol, ethanol, 1,4-dioxane, tetrahydrofuran, chloroform, methylene chloride or diethyl ether, in the atmospheric air or under an inert atmosphere of argon, helium or carbon dioxide gas at a temperature of –40° to +120° C., preferably 0° to 60° C., for 10 minutes to 240 hours, preferably 1–48 hours, preferably with agitation.

The phospholipid derivatives represented by the general formula (1) with p=1, namely, those of the general formula (1-2), can be produced easily, for example, in such a manner,

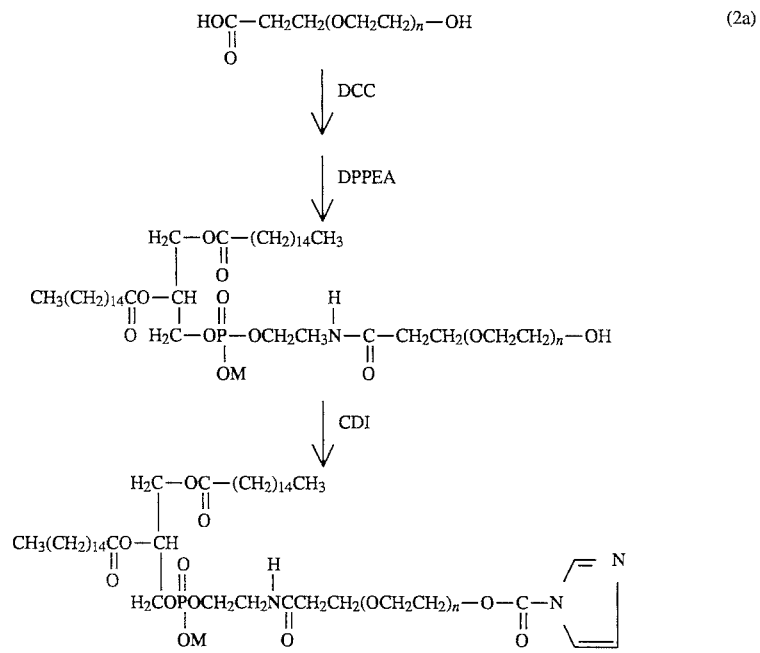

(2a)

The phospholipid derivatives can also be produced easily in an alternative way, for example, by preparing an active product of the (poly)oxyalkylene derivative by converting its carboxyl group into acid chloride group using, for example, thionyl chloride or isobutyl chloroformate, or into an active ester using, for example, succinimide or N,N'-carbonyldiimidazole, and reacting this active product with a phosphatidylethanolamine, whereupon the resulting product is reacted with CDI. By this, phospholipid derivatives of general formula (1-1) with q=1 to 4 are obtained.

The phospholipid derivatives can be produced easily in a further alternative way by reacting a phosphatidylethanolamine with a (poly)oxyalkylene derivative having at its both that an α-hydro-ω-hydroxy(poly)oxyethylene is reacted with a dicarboxylic acid anhydride, such as succinic anhydride (SAN), in a mole proportion of 1:1 to 1:0.01, followed by purification by, for example, treatment on a column, to obtain a polyoxyethylene derivative having a carboxyl group at its one end and a hydroxyl group at the other end, whereupon this polyoxyethylene derivative is reacted with a phosphatidylethanolamine in a similar manner as in the production of the phospholipid derivative of the general formula (1-1). The reaction sequence for this is shown in the following reaction scheme (2b), in which M and n have the same meanings as those given previously.

(2b)

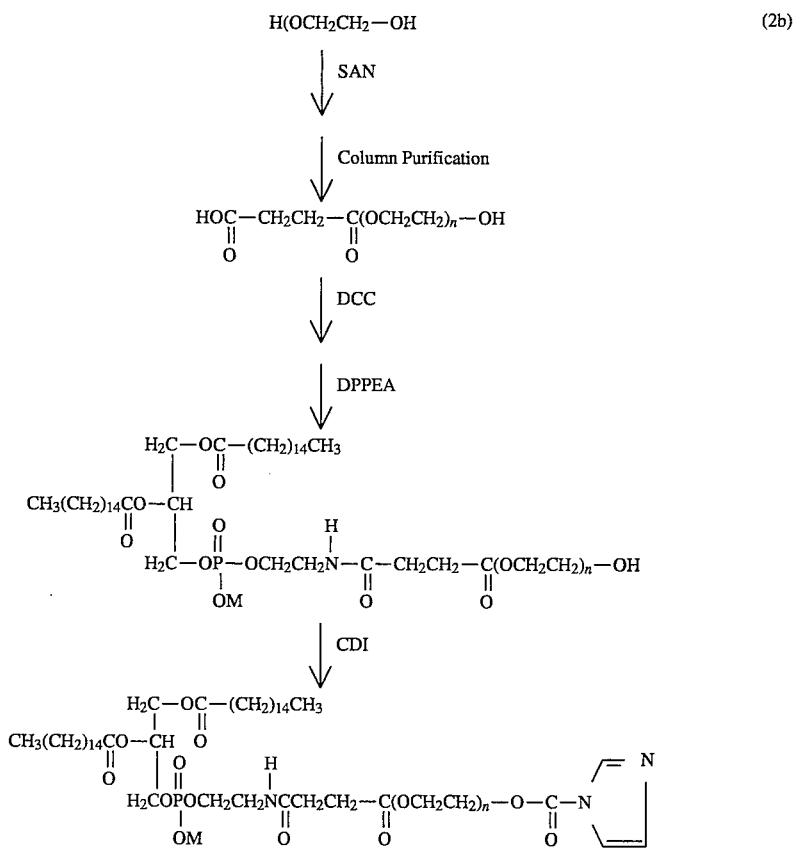

The phospholipid derivatives represented by the general formula (1) with p=0, namely those of the general formula (1-3), can be produced easily, for example, by a two-step reaction in the following way:

In the first step reaction, a phosphatidyl (poly)alkylene glycol is synthesized by reacting a phospholipid with an α-hydro-ω-hydroxy (poly)oxyalkylene in the presence of an enzyme phospholipase D (PLase-D). As the phspholipase D to be used here, either a commercial product or an extracted and purified product obtained by the method described in J. Biol. Chem., 242, 477–484 (1967) can be employed. As the phospholipid, for example, phosphatidylethanolamine, phosphatidylcholine, phosphatidylserine, phosphatidylinositol, phosphatidylglycerol or phosphatidic acid, can be employed. Phospholipase D may preferably be used in an amount of, though not limited specifically, 100 to 500 units per gram of the phospholipid. The mixing proportion of the phospholipid and the α-hydro-ω-hydroxy (poly)oxyalkylene may preferably be 5–100 moles of the α-hydro-ω-hydroxy (poly)oxyalkylene per mole of the phospholipid.

The reaction may be carried out preferably in an aqueous medium, such as an acetate buffer or a carbonate buffer, or in a mixed medium composed of such an aqueous medium and an organic solvent, such as chloroform, benzene, toluene, tetrahydrofuran or acetonitrile. The reaction may be effected at a temperature of 0°–80° C., preferably 30°–40° C., for 10 minutes–170 hours, preferably for 30 minutes to 24 hours.

The phosphatidyl (poly)alkylene glycol product obtained in this manner may be used for the second step reaction as such or after isolation and purification by, for example, recrystallization, treatment on a column, treatment by adsorption, ion-exchange, gel filtration, ultrafiltration or dyalysis.

In the second step reaction, the contemplated phospholipid derivative is synthesized by reacting the phosphatidyl (poly)alkylene glycol with N,N'-carbonyldiimidazole or a substituted product thereof. While there is no special limitation in the mixing proportion of the starting reactants, it is preferable to use 0.1–100 moles, preferably 1–10 moles of N,N'-carbonyl diimidazole or its substitution product per mole of the phosphatidyl (poly)alkylene glycol.

The reaction may preferably be carried out in an organic solvent, such as chloroform, benzene, toluene, tetrahydrofuran or acetonitrile. The reaction temperature may preferably be in the range from −100° C. to +100° C., preferably from 0° C. to 40° C., and the reaction duration may be in the range from 1 minute to 48 hours, preferably from 10 minutes to 6 hours.

The reaction course using an α-hydro-ω-hydroxy polyoxyethylene as the α-hydro-ω-hydroxy (poly)oxyalkylene is given in the following reaction scheme (3), in which $R^1C(=O)$, $R^2C(=O)$, M and n are the same with those of the general formulae given above and PL-PEG represents phosphatidyl (poly)ethylene glycol:

Phospholipid (3)

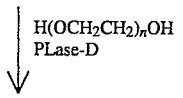

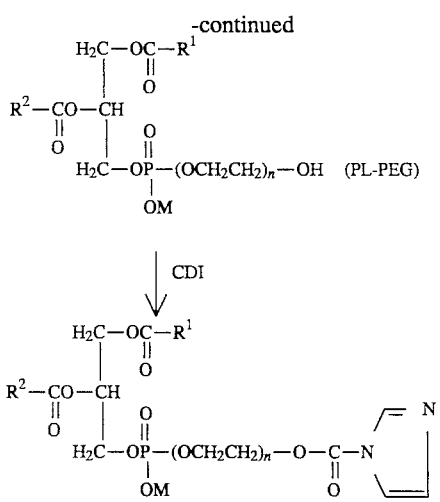

-continued (PL-PEG)

↓ CDI

After the phospholipid derivative represented by the general formula (1) has been produced as above, it can be used as, for example, a component for forming a vesicle, in the form of the reaction mixture as such or after it is isolated and purified from the reaction mixture by distillation, recrystallization, reprecipitation, treatment by adsorption, treatment on column, gel filtration, ultrafiltration, dialysis, ion-exchange or thin layer chromatography.

The phospholipid derivatives represented by the general formula (1) having oxycarbonylimidazole group or its substituted group will react easily with various functional substances having functional group(s) of amino, hydroxyl and/or thiol and so on to build up a covalent bond, since oxycarbonylimidazole group has a high tendency to react with these functional groups, especially with primary amino group. Thus, the phospholipid derivatives according to the present invention are those exhibiting a reactivity which, when used as a component for forming a vesicle such as liposome, can impart to the resulting vesicle a high ability to react with the functional groups mentioned above. Therefore, the phospholipid derivatives according to the present invention can be used as a reactive vesicle-forming agent for producing a reactive vesicle.

Thus, the reactive vesicle-forming agent according to the present invention comprises the phospholipid derivative represented by the general formula (1) which can be used each solely or in combination of two or more of them or, further, in combination with other vesicle-forming component(s), for example, other phospholipids, such as soybean lecithin and yolk lecithin, cholesterol, Intralipid (Trademark, Otsuka Pharmaceuticl Co., Ltd.), soybean oil and safflower oil, to form a reactive vesicle, such as a reactive liposome, reactive fatty emulsion or a reactive micell. These vesicles may be produced by known methods.

Various functional substances can be introduced into the reactive vesicle obtained by using the phospholipid derivative according to the present invention, by a covalent bond by making use of the oxycarbonylimidazole group or its substituted group in the compound represented by the general formula (1) as a functional group.

Below, the reactive vesicle produced from the phospholipid derivative represented by the general formula (1) is explained in detail for each specific one obtained.

A reactive liposome as a representative reactive vesicle comprises the phospholipid derivative represented by the general formula (1) as a membrane-forming component (vesicle-forming component). The content of the phospholipid derivative represented by the general formula (1) may preferably be in the range of 0.01–50 mole %, preferably 0.5–30 mole %, based on the total moles of the phospholipid derivative according to the present invention and other membrane-forming components. If this content is less than 0.01 mole %, the expected effect will be low and, if it exceeds over 50 mole %, the stability of the liposome becomes decreased and such a content is not chosen in general. The phospholipid derivatives represented by the general formula (1) may be used each solely or in combination of two or more of them.

As other membrane-forming components to be used in combination with the phospholipid derivative represented by the general formula (1), those which have hitherto found their application for the membrane-forming component of the liposome can be employed without limitation. Concrete examples therefor include phospholipids and polymerizable phospholipids having unsaturated group(s) in the acyl group of fatty acids, such as diphosphatidylglycerol, cardiolipin, phosphatidylinositol, phosphatidylserine, phosphatidylethanolamine, soybean lecithin, yolk lecithin, phosphatidylcholine and phosphatidylglycerol; glycolipids, such as sulfoxyribosyldiglyceride, digalactosyldiglyceride and lactosyldiglyceride; nonpolar lipids, such as cholesterols; and others, such as nonionic surfactants, phosphatidyl polyethylene glycol and reaction products of phosphatidylethanolamine with α-hydro-ω-hydroxy polyoxyethylene such as those described in Biochem. Biophys. Acta, 1066, 29–36 (1991) as well as mixtures of them.

Reactive liposomes can be produced by various methods, for example, by dissolving a phospholipid derivative represented by the general formula (1) and, if necessary, other membrane-forming components, such as other phospholipids such as lecithin, or cholesterols, in an adequate medium, such as an organic solvent, and processing the resulting solution into a liposome by a known technique, such as extrusion method, vortex mixer method, ultrasonication method, surfactant-removal method, reversed phase evaporation, ethanol introducing method, prevesicle method, french-press method, W/O/W-emulsion method, annealing method or freeze thawing method. By choosing an appropriate technique among them, reactive liposomes having various sizes and morphologies can be produced.

The reactive liposome obtained as above has an oxycarbonylimidazole group or its substituted group suspending from the both side surfaces of the resulting liposome membrane under intermediation by a spacer consisting of a (poly)oxyalkylene chain, so that it can afford to fix various functional substances having functional group(s), such as amino, hydroxyl, thiol and the like, in particular, primary amino group, easily and efficiently onto the bimolecular membrane of the liposome through a chemical bond, such as urethane bond, carbonate bond, thiocarbonate bond or the like, under intermediation by a spacer consisting of a (poly-)oxyalkylene chain.

As the functional substances to be fixed onto the liposome membrane, various substances having, or provided by introduction with, functional groups such as those mentioned above, namely, amino, in particular primary amino, hydroxyl, thiol and so on, may be enumerated. Concrete examples thereof include labelling compounds, such as pigments, dyestuffs, radioactive labelling compounds, fluorescent compounds, chemiluminescent compounds and electrode-sensitive compounds; external stimulation-responsible compounds, such as light-responsible compounds, pH-responsible compounds and heat-responsible compounds;

physiological substances, such as proteins including enzymes and antibodies, sugars, lipids, glycoproteins, glycolipids and hormones; and various medicaments. Among them, functional substances having primary amino groups are of particular interest.

The reaction to fix the functional substance onto the reactive liposome membrane can be realized easily in various ways including a one-step technique, which comprises subjecting the reactive liposome and the functional substance to a reaction with each other in an adequate reaction medium, such as an aqueous medium, for example, physiological saline, phosphate buffer, carbonate buffer, tris buffer, acetate buffer or borate buffer, or further, a mixture of these aqueous medium with an organic solvent, such as methanol, ethanol, acetone, acetonitrile, tetrahydrofuran, 1,4-dioxane, dimethylformamide, dimethylacetamide, dimethylsulfoxide and pyrrolidone, at a temperature from −10° to +120° C. and, in the case of reaction with an amino group, at a temperature, preferably, from 0° to 60° C., in particular, from 0° to 40° C., and, in the case of reaction with hydroxyl or thiol group, at a temperature, preferably, from 40° to 120° C., for a reaction period in the range from 5 minutes to 1,000 hours, preferably from 30 minutes to 72 hours under agitation. Reaction conditions other than those given above are undesirable, since the stability of the liposome will be lower.

A reaction sequence of the fixation of a functional substance having an amino group with the liposome membrane may be shown schematically by the following reaction scheme (4) in which $R^3$, OA and n are the same as those explained previously, Lip indicates the liposome and Y indicates the residue of the functinal substance, respectively:

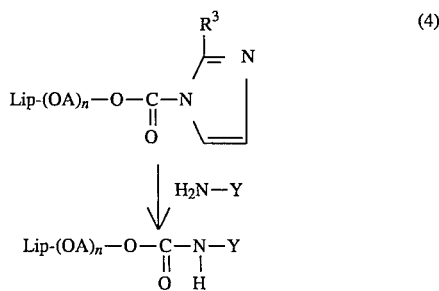

The reactive liposome vesicle according to the present invention can enclose therein various materials by a known technique, as in the conventional cellular liposomes. The material to be enclosed therein may be, for example, labelling compounds, such as pigments, dyestuffs, radioactive labelling compounds, fluorescent compounds and chemiluminescent compounds; external stimulation-responsible compounds, such as light-responsible compounds, pH-responsible compounds, heat-responsible compounds and electrode-susceptible compounds; physiologically active substances, such as proteins including enzymes and antibodies, sugars, lipids, glycoproteins, glycolipids and hormones; drugs, such as medicaments; and water-soluble high polymeric materials, such as polyacrylamides, polyvinyl alcohols, α-hydro-ω-hydroxy polyoxyethylene and hyaluronic acid.

The reactive vesicle according to the present invention after having been subjected to the fixation reaction or enclosure step, can be purified, if necessary, by a known technique, such as gel filtration, ultrafiltration, dialysis, centrifugation or still sedimentation separation.

The resulting functional substance-fixed liposome has, thus, the functional substance fixed at the top end of the (poly)oxyalkylene chain, so that the function intrinsic of the functional substance can be revealed sufficiently without suffering from any hindering action of the (poly)oxyalkylene chain. Here, it is expectable that the reactive vesicle will reveal also the effect of incorporation of the (poly)oxyalkylene chains in the liposome membrane proposed in the prior technique, such as increase in the maintaining performance of the vesicle concentration in blood, non-immunogenicity, prevention of leaking out of the material enclosed therein and so on.

Thus, the reactive liposome obtained by using the phospholipid derivative according to the present invention and the functional substance-fixed liposome derived therefrom can be utilized for various functional liposomes and carriers therefor, such as, for drug carrier for the drug delivery system to transport a medicament to the target site, for producing liposomal preparations, testing drugs, diagnostic drugs, sensors, fixed catalysts, bioreactors, elements for bioelectronics and substitutes for microcapsules.

When a polymerizable other phospholipid derivative is employed as another membrane-forming component together with the reactive phospholipid derivative represented by the general formula (1) in producing the reactive liposomal vesicle, a polymerizable reactive liposomal vesicle can be obtained. For the polymerizable phospholipid, known ones can be employed, for example, 1,2-di(2,4-octadecadienoyl)-glycero-3-phosphocholine and those which are described in S. Shimano, J. Sunamoto and K. Inoue; "Liposomes", pp 313–351 (1988), issued from Nankodo. Among them, 1,2-di(2,4-octadecadienoyl)-glycero-3-phosphocholine is preferred.

The polymerizable liposome can easily be subjected to polymerization by, for example, irradiation of UV-rays, γ-rays and electron beams, using a redox initiator or heating in the presence of an azo-initiator, an organic peroxide or ammonium persulfate. The resulting polymerized liposome has a superior stability and, therefore, can be used in the form of aqueous suspension as such or for preparing a pulverous product by, for example, freeze drying, to serve for a stable application.

For a reactive vesicle other than liposome, a reactive fatty emulsion may be employed, which is prepared by emulsifying an oily mixture containing a phospholipid derivative represented by the general formula (1), a vegetable oil component, such as soybean oil and safflower oil, and an unmodified phospholipid component (another phospholipid component), such as soybean lecithin and yolk lecithin, in an aqueous emulsion medium together with other optionally employed additives, such as Intralipid (Trademark, Ohtsuka Pharmac. Co.), emulsifying assistants, stabilizers, isotonizing agents, oil-soluble medicaments and oil-soluble physiological substances. In these rective fatty emulsions, the phospholipid derivative of the general formula (1) and other membrane-forming components are drawn up towards the interface between the oil phase of the oil droplets and the aqueous phase surrounding it and accumulate there to form a vesicle.

The content of the phospholipid derivative represented by the general formula (1) in the oil mixture may preferably amount to 0.01–50 mole %, in particular, 0.5–30 mole %. The reactive fatty emulsion can be prepared by a known method. For example, the phospholipid derivative of the general formula (1), the vegetable oil component and the unmodified phospholipid component are brought together under addition of, if necessary, other additives and the resulting mixture is then subjected to a rough emulsification on, for example, a homomixer with heating and with an addition of water, whereupon the resulting mixture is homogenized into a finished emulsion by, for example, a pressure-jet homogenizer of, such as, Manton-Gaulin type.

On the so-obtained reactive fatty emulsion, various functional substances, such as those used in the reactive liposomal vesicles, can be fixed easily in the same manner. Therefore, the reactive fatty emulsion can be used for preparing drug carriers, testing drugs, diagnostic drugs, sensors and fixed catalysts.

As a reactive vesicle other than those described above, reactive micell can be employed which contains the phospholipid derivative represented by the general formula (1), wherein the micell may be composed of only the phospholipid derivative of the general formula (1) or composed of a combination thereof with, for example, other micell-forming components, such as lecithin or other phospholipids, cholesterols and so on. The reactive micell can be produced by introducing the phospholipid derivative of the general formula (1) solely or in a form of a mixture with other micell-forming component(s) into an aqueous phase in an amount sufficient to exceed above the micell forming concentration. The reactive micells can also be used for fixing thereon various functional substances in the same manner as in the reactive fatty emulsion in order to use for similar applications.

As detailed above, the phospholipid derivative according to the present invention is a novel and useful substance. By employing the phospholipid derivative according to the present invention as a component of the reactive vesicle-forming agent, it is able to introduce into the vesicle (poly)oxyalkylene chains and to fix on the top ends of these (poly)oxyalkylene chains a larger amount of various functinal substances by a covalent bond easily and efficiently.

The reactive vesicle-forming agent according to the present invention has the structure of the general formula (1), so that (poly)oxyalkylene chains can be introduced into the reactive vesicle containing it and the functional substances may easily be fixed to the top ends of these (poly)oxyalkylene chains efficiently by a covalent bond in a larger amount.

PREFERRED EMBODIMENT OF THE INVENTION

Below, the present invention will further be described by way of concrete examples, while these Examples should not be understood as limiting the present invention.

EXAMPLE 1-1

1.0 g (0.3 mmol) of an α-hydro-ω-carboxyl polyoxyethylene (MW=about 3,000, average addition mole number= about 65) and 68 mg (0.3 mmol) of N,N'-dicyclohexylcarbodiimide were dissolved in 10 ml of ethyl acetate and the solution was stirred at 5° C. for 1 hour. Thereto was then added 10 ml of a ethyl acetate solution containing dissolved therein 217 mg (0.3 mmol) of dipalmitoyl-glycero-phosphoethanolamine and the mixture was stirred for further 6 hours and the mixture was then stood still overnight at 0° C., whereupon the deposited matter was removed by filtration. Then, 49 mg (0.3 mmol) of N,N'-carbonyl-diimidazole were added to the filtrate and the mixture was stirred for 1 hour at room temperature, whereupon the resulting reaction mixture was poured into 100 ml of diethyl ether and the precipitate was separated by filtration to obtain the contemplated reactive phospholipid derivative of the formula (5) given below as a white powdery product (yield=88%). The progress of the reaction was monitored by IR spectrum (KBr method) by detecting the disappearance of the remaining amino groups in the phosphatidylethanolamine ($N^+H_2$-stretching; 3,000 $cm^{-1}$) and the formation of amide bonds (C=O-stretching; 1,647 $cm^1$) for the intermediate product, on the one hand, and detecting the disappearance of the terminal hydroxyl groups in the polyoxyethylene derivative (OH-stretching; 3,428 $cm^{-1}$) and the formation of the oxycarbonylimidazole bonds (C=O-stretching; 1,760 $cm^{-1}$) for the target product, on the other hand.

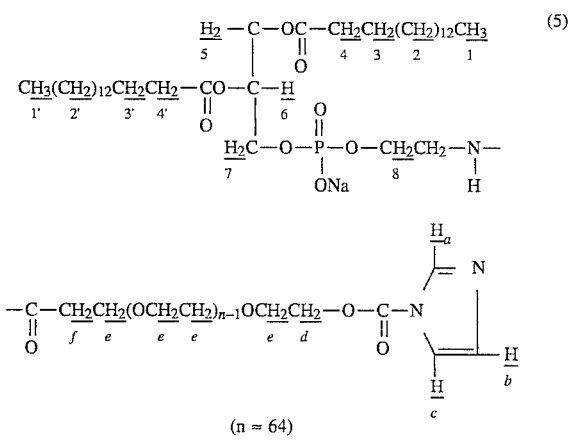

The observed NMR- and IR-spectra of the above reactive phospholipid derivative were as given below:

$^1$H-NMR ($CDCl_3$/TMS, δ: ppm, 270 MHz) 8.14 (a; s, 1H) 7.43 (b; t, 1H, J=1.3) 7.08 (c; t, 1H, J=0.8) 5.23 (6; m, 1H) 4.67 (d; t, 2H, J=2.5) 4.29 (8; m, 2H) 4.00 (5, 7; m, 4H) 3.64 (e; m, ca. 255H) 3.06 (f; t, 2H, J=7.3) 2.31 (4, 4'; m, 4H) 1.60 (3, 3'; m, 4H) 1.26 (2, 2'; m, 48H) 0.88 (1, 1'; t, 6H, J=6.4)

IR (KBr, $cm^{-1}$) 1760 (oxycarbonylimidazole bond: C=O-stretch.) 1728 (ester: C=O-stretching) 1647 (amide: C=O-stretching) 1526 (amide: NH-deformation vibration) 1465 (C—H-deformation vibration)

EXAMPLE 1-2

The procedures of Example 1-1 were pursued with the exception that an α-carboxymethyl-ω-hydroxy polyoxyethylene (average addition mole number=about 35) was used as the polyoxyalkylene derivative, whereby a reactive phospholipid derivative of the following formula (6) was obtained.

$$\begin{array}{c} \underline{H}_2 - \underline{C} - O\underline{C} - \underline{CH_2CH_2(CH_2)_{12}CH_3} \\ 5 \quad | \quad \parallel \quad 4 \quad 3 \quad 2 \quad 1 \\ \quad \quad O \\ CH_3(CH_2)_{12}C\underline{H_2CH_2} - \underline{C}O - \underline{C} - \underline{H} \\ 1' \quad 2' \quad 3' \quad 4' \quad \parallel \quad | \quad 6 \quad O \\ \quad \quad O \quad \quad \parallel \\ \quad \quad H_2C - O - P - O - \underline{CH_2CH_2} - N - \\ \quad \quad 7 \quad | \quad 8 \quad \parallel \\ \quad \quad ONa \quad \quad H \end{array} \quad (6)$$

-continued

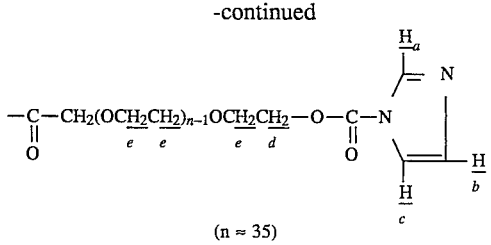

(n ≈ 35)

The observed NMR- and IR-spectra of the above reactive phospholipid derivative were as given below:

$^1$H-NMR (CDCl$_3$/TMS, δ: ppm, 270 MHz) 8.14 (a; s, 1H) 7.43 (b; t, 1H, J=1.3) 7.08 (c; t, 1H, J=0.8) 5.23 (6; m, 1H) 4.67 (d; t, 2H, J=2.5) 4.29 (8; m, 2H) 4.00 (5, 7; m, 4H) 3.64 (e; m, ca. 140H) 2.31 (4, 4'; m, 4H) 1.60 (3, 3'; m, 4H) 1.26 (2, 2'; m, 48H) 0.88 (1, 1'; t, 6H, J=6.4)

IR (KBr, cm$^{-1}$) 1760 (oxycarbonylimidazole bond: C=O-stretch.) 1728 (ester: C=O-stretching) 1647 (amide: C=O-stretching) 1526 (amide: NH-deformation) 1465 (C—H-deformation)

EXAMPLE 1-3

The procedures of Example 1-1 were pursued with the exception that a polyoxyalkylene derivative of the following formula (7)

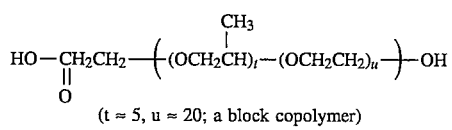

(t ≈ 5, u ≈ 20; a block copolymer)

was used, whereby a reactive phospholipid derivative of the following formula (8) was obtained.

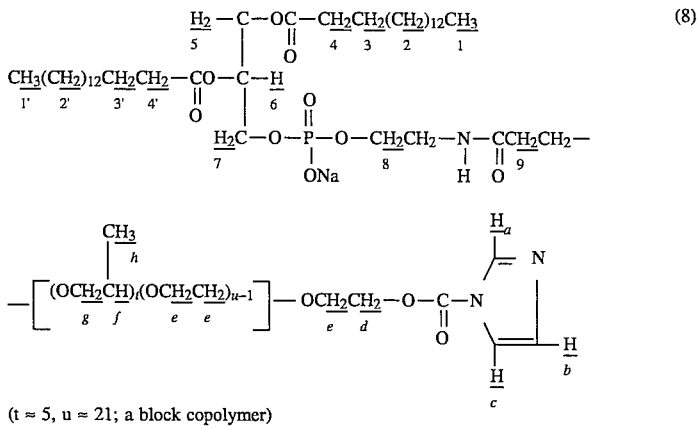

(t ≈ 5, u ≈ 21; a block copolymer)

The observed NMR- and IR-spectra of the above reactive phospholipid derivative were as given below:

$^1$H-NMR (CDCl$_3$/TMS, δ: ppm, 270 MHz) 8.14 (a; s, 1H) 7.43 (b; t, 1H, J=1.3) 7.08 (c; t, 1H, J=0.8) 5.23 (6; m, 1H) 4.67 (d; t, 2H, J=2.5) 4.29 (8; m, 2H) 4.00 (5, 7; m, 4H) 3.60 (e,f,g; m, ca. 95H) 3.06 (j; t, 2H, J=7.3) 2.31 (4, 4'; m, 4H) 1.60 (3, 3'; m, 4H) 1.26 (2, 2'; m, 48H) 1.12 (h; m, ca. 15H) 0.88 (1, 1'; t, 6H, J=6.4)

IR (KBr, cm$^{-1}$) 1760 (oxycrbonylimidzole bond: C=O-stretching) 1728 (ester: C=O-stretching) 1647 (amide: C=O-stretching) 1526 (amide: NH-deformation) 1465 (C—H-deformation)

EXAMPLE 1-4

1.0 g (0.3 mmol) of an α-hydro-ω-carboxyl polyoxyethylene (MW=about 3,000, average addition mole number= about 65) and 68 mg (0.3 mmol) of N,N'-dicyclohexylcarbodiimide were dissolved in 10 ml of ethyl acetate and the solution was stirred at 5° C. for 1 hour. Thereto was then added 10 ml of a ethyl acetate solution containing dissolved therein 217 mg (0.3 mmol) of dipalmitoyl-glycero-phosphoethanolamine and the mixture was stirred for further 6 hours and the mixture was then stood still overnight at 0° C., whereupon the deposited matter was removed by filtration. Then, 49 mg (0.3 mmol) of N,N'-carbonyldiimidazole were added to the filtrate and the mixture was stirred for 1 hour at room temperature, whereupon the resulting reaction mixture was poured into 100 ml of hexane and the precipitate was separated by filtration to obtain the contemplated reactive phospholipid derivative of the formula (9) given below as a white powdery product (yield=88%). The progress of the reaction was monitored by IR spectrum (KBr method) by detecting the disappearance of the remaining amino groups in the phosphatidylethanolamine (N$^+$H$_2$-stretching; 3,000 cm$^{-1}$) and the formation of amide bonds (C=O-stretching; 1,647 cm$^1$) for the intermediate product, on the one hand, and detecting the disappearance of the terminal hydroxyl groups in the polyoxyethylene derivative (OH-stretching; 3,428 cm$^{-1}$) and the formation of the oxycarbonylimidazole bonds (C=O-stretching; 1,760 cm$^{-1}$) for the target product, on the other hand.

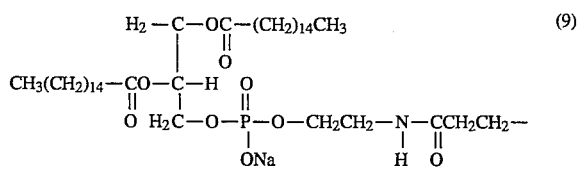

-continued

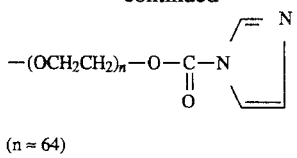

(n ≈ 64)

EXAMPLE 1-5

9 g (3 mmol) of an α-hydro-ω-hydroxy polyoxyethylene (MW=ca. 3,000) and 1.36 g (6 mmol) of N,N'-carbonyldiimidazole were dissolved in 30 ml of chloroform and the solution was stirred at 5° C. for 1 hour. Thereto was then added 1 ml of a chloroform solution containing dissolved therein 217 mg (0.3 mmol) of dipalmitoyl-glycero-phosphoethanolamine and the mixture was agitated for further 6 hours. The resulting reaction mixture was treated on a silica gel column (solvent: 20% methanol/chloroform) to isolate and purify the reaction product, which was then subjected to freeze drying after the solvent was replaced by benzene, whereby the contemplated product of the reactive phospholipid derivative represented by the following formula (10) was obtained as a white powder (yield=74%).

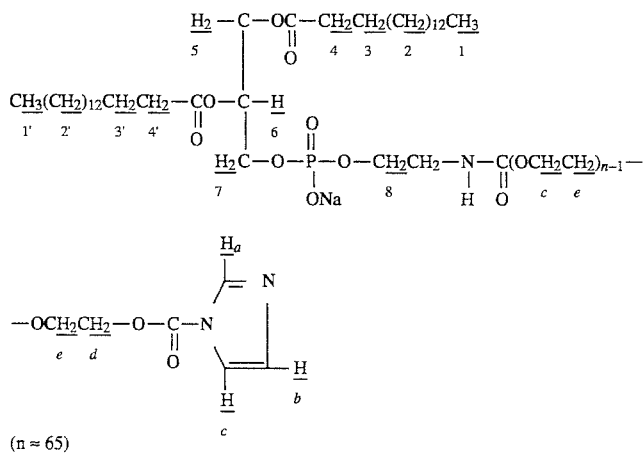

(10)

(n ≈ 65)

The observed NMR- and IR-spectra of the above reactive phospholipid derivative were as given below:

$^1$H-NMR (CDCl$_3$/TMS, δ: ppm, 270 MHz) 8.14 (a; s, 1H) 7.43 (b; t, 1H, J=1.3) 7.08 (c; t, 1H, J=0.8) 5.23 (6; m, 1H) 4,67 (d; t, 2H, J=2.5) 4.29 (8; m, 2H) 4.00 (5, 7; m, 4H) 3,64 (e; m, ca, 255H) 2.31 (4, 4'; m, 4H) 1.61 (3, 3'; m, 4H) 1.26 (2, 2'; m, 48H) 0.88 (1, 1'; t, 6H, J=6.4)

IR (KBr, cm$^{-1}$) 1760 (oxycarbonylimidazole bond: C=O-stretch,) 1526 (amide: NH-deformation) 1465 (C—H-deformation)

EXAMPLE 2-1

40 ml of a chloroform solution containing dissolved therein 0.5 g (0.65 mmol) of dipalmitoyl-glycero-phosphocholine and 5 g (1.7 mmol) of an α-hydro-ω-hydroxy polyoxyethylene (MW=ca. 2,000, average addition mole number=about 45) were mixed with 20 ml of 1M acetic acid buffer solution (pH 5.6) containing dissolved therein 40 units of phospholipase D (Toyo Jozo CO., Ltd.) and the mixture was stirred at 40° C. for 12 hours to react them. Then, the reaction mixture was neutralized using 0.1N aqueous solution of sodium hydroxide and the organic phase was concentrated under a reduced pressure. The resulting reaction mixture was subjected to a chromatographic fractionation on a silica gel column (20% methanol/chloroform) and the target product was concentrated and dissolved in a small amount of chloroform, from which the target product dipalmitoyl-glycero-phosphopolyethylene glycol was obtained by re-precipitation with diethyl ether (yield=30%).

100 mg (0.27 mmol) of the so-obtained dipalmitoyl-glycero-phosphopolyethylene glycol and 87 mg (0.54 mmol) of N,N'-carbonyldiimidazole were introduced in 10 ml of dried chloroform and the mixture was stirred at room temperature for 6 hours. The resulting reaction mixture was subjected to re-precipitation in 100 ml of diethyl ether, whereby a reactive phospholipid derivative of the following formula (11) was obtained (yield=92%).

The progress of the reaction was monitored by IR spectrum (KBr method) by detecting the disappearance of the terminal hydroxyl groups in the α-hydro-ω-hydroxy polyoxyethylene (OH-stretching; 3,428 cm$^{-1}$) and the formation of the oxycarbonylimidazole bonds (C=O-stretching; 1,760 cm$^{-1}$) for the target product.

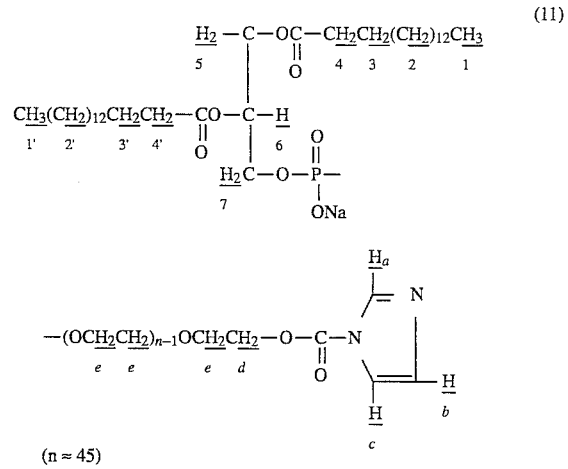

(n ≈ 45)

The purified product was confirmed by $^1$H-NMR- and

IR-spectra, the results of which were as given below:

$^1$H-NMR (CDCl$_3$/TMS, δ: ppm, 270 MHz) 8.14 (a; s, 1H) 7.43 (b; t, 1H) 7.08 (c; s, 1H) 5.23 (6; m, 1H) 4.67 (d; t, 2H, J=2.5) 3.65 (e; m, ca. 180H) 2.31 (4, 4'; m, 4H) 1.60 (3, 3'; m, 4H) 1.29 (2, 2'; m, 48H) 0.90 (1, 1'; m, 6H)

IR (KBr, cm$^{-1}$) 1760 (oxycarbonylimidazole bond: C=O-stretch.) 1728 (ester: C=O-stretching)

EXAMPLE 2-2

The procedures of Example 2-1 were pursued with the exception that the α-hydro-ω-hydroxy polyoxyethylene was replaced by one having a molecular weight of about 5,000 (average addition mole number=about 115), whereby a reactive phospholipid derivative of the following formula (12) was obtained as the target product.

7.43 (b; s, 1H) 7.08 (c; s, 1H) 5.23 (6; m, 1H) 4.67 (d; t, 2H, J=2.5) 4.00 (5, 7; m, 4H) 3.65 (e; m, ca. 455H) 2.31 (4, 4'; m, 4H) 1.60 (3, 3'; m, 4H) 1.29 (2, 2'; m, 48H) 0.90 (1, 1'; m, 6H)

IR (KBr, cm$^{-1}$) 1760 (oxycarbonylimidazole bond: C=O-stretch.) 1728 (ester: C=O-stretching)

EXAMPLE 2-3

The procedures of Example 2-1 were pursued with the exception that the α-hydro-ω-hydroxy polyoxyethylene was replaced by one having an added block-structure of $$(\text{oxyethylene})_p(\text{oxypropylene})_q(\text{oxyethylene})_R$$

in which p≈20, q≈5 and r≈20, whereby a reactive phospholipid derivative of the following formula (13) was obtained as the target product.

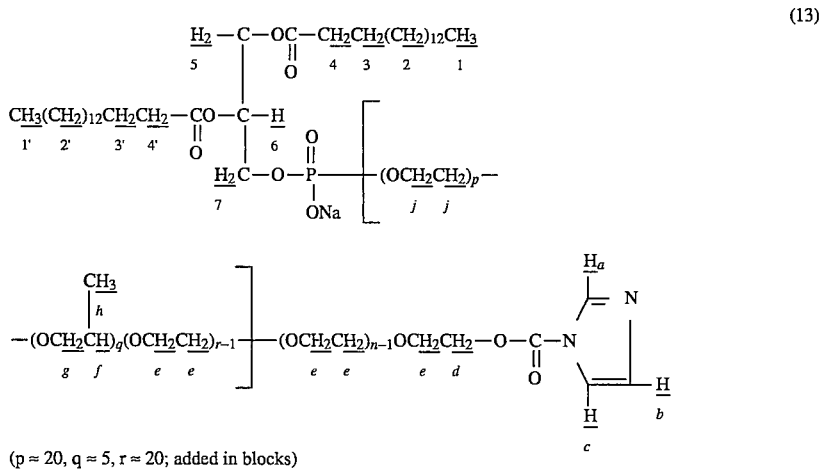

(p ≈ 20, q ≈ 5, r ≈ 20; added in blocks)

(13)

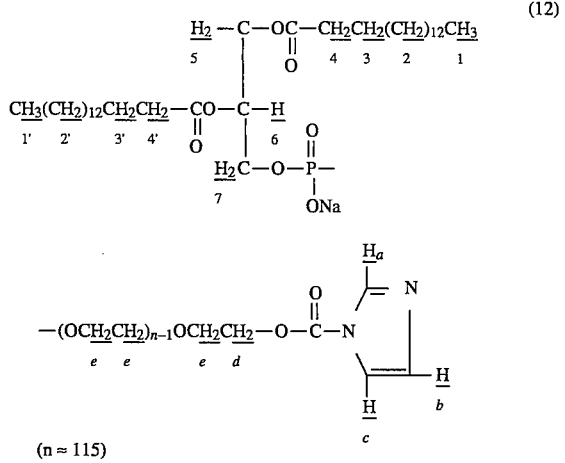

(n ≈ 115)

(12)

The purified product was confirmed by $^1$H-NMR- and IR-spectra, the results of which were as given below:

$^1$H-NMR (CDCl$_3$/TMS, δ: ppm, 270 MHz) 8.14 (a; s, 1H)

The purified product was confirmed by $^1$H-NMR-spectra, the results of which were as given below:

$^1$H-NMR (CDCl$_3$/TMS, δ: ppm, 270 MHz) 8.14 (a; s, 1H) 7.43 (b; t, 1H, J=1.3) 7.08 (c; t, 1H, J=0.8) 5.23 (6; m, 1H) 4.67 (d; t, 2H, J=2.5) 4.00 (5, 7; m, 4H) 3.60 (e,f,g,j; m, ca. 190H) 2.31 (4, 4'; m, 4H) 1.60 (3, 3'; m, 4H) 1.26 (2, 2'; m, 48H) 1.12 (h; m, 15H) 0.88 (1, 1'; t, 6H, J=6.4)

EXAMPLE 3-1

20 mg (26 μmol) of yolk phosphatidylcholine and 3.9 mg (10 μmol) of cholesterol were placed in an eggplant type flask together with 10% by weight, based on the above two compounds, (2.4 mg: 0.7 μmol) of a reactive phospholipid derivative obtained in Example 1-4 and the mixture was dissolved in 2 ml of benzene, whereupon the mixture was subjected to freeze drying. Then, 1 ml of physiological saline was added thereto and, by treatment by a bath-type ultrasonication and using a vortex mixer, a mixture of multilayer liposomes was obtained. This mixture was then processed by an extruder by passing it through a series of three polycarbonate membranes of 3.0 μm, 1.0 μm and 0.2 μm successively in this order, whereby a reactive liposome as a large unilamellar vesicle was obtained. By determining the particle size of the resulting reactive liposome with a laser scattering size distribution meter [NICOMP 370HPL (Trademark) of NICOMP], an average particle size of 255 nm (with CV value of 18%) was found.

EXAMPLE 3-2

The procedures of Example 3-1 were pursued with the exception that a reactive phospholipid derivative of the following formula (14)

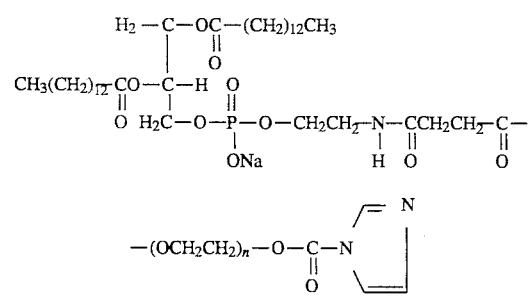

(n ≈ 10)

was used in an amount of 5% by weight (1.0 μmol), whereby a reactive liposome with an average particle size of 278 nm and a CV value of 23% was obtained.

EXAMPLE 3-3

The procedures of Example 3-1 were pursued with the exception that a reactive phospholipid derivative of the following formula (15)

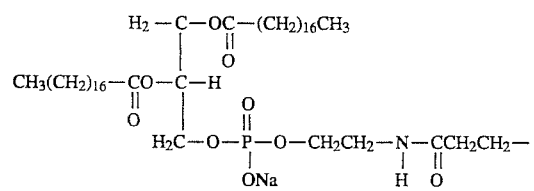

(n ≈ 30)

was used in an amount of 30% by weight (3.6 μmol), whereby a reactive liposome with an average particle size of 248 nm and a CV value of 25% was obtained.

EXAMPLE 3-4

The procedures of Example 3-1 were pursued with the exception that a reactive phospholipid derivative of the following formula (16)

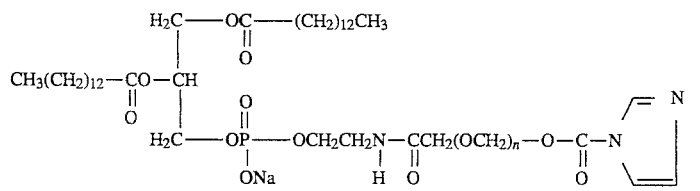

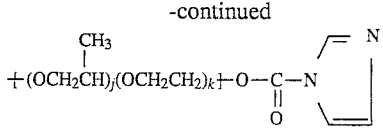

(j ≈ 10, k ≈ 25; a random copolymer)

was used in an amount of 1% by weight (0.1 μmol), whereby a reactive liposome with an average particle size of 250 nm and a CV value of 21% was obtained.

EXAMPLE 3-5

The procedures of Example 3-1 were pursued with the exception that a reactive phospholipid derivative of the following formula (17)

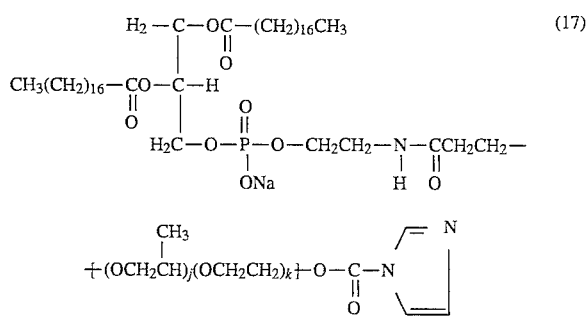

(j ≈ 10, k ≈ 15; a block copolymer)

was used in an amount of 5% by weight (0.6 μmol), whereby a reactive liposome with an average particle size of 250 nm and a CV value of 21% was obtained.

EXAMPLE 3-6

The procedures of Example 3-1 were pursued with the exception that a reactive phospholipid derivative of the following formula (18)

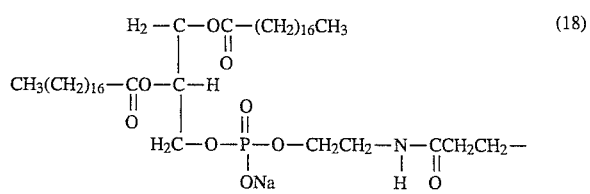

-continued

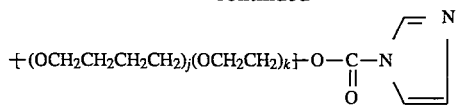

(j ≈ 5, k ≈ 278; a block copolymer)

was used in an amount of 5% by weight (0.1 μmol), whereby a reactive liposome with an average particle size of 291 nm and a CV value of 24% was obtained.

EXAMPLE 3-7

The procedures of Example 3-1 were pursued with the exception that a reactive phospholipid derivative of the following formula (19)

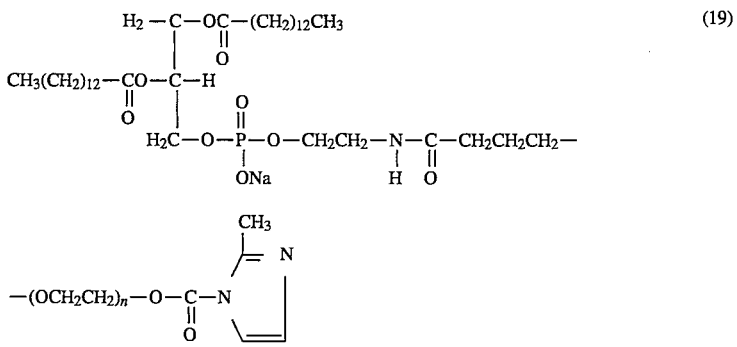

(19)

(n ≈ 11)

was used in an amount of 20% by weight (4.0 μmol), whereby a reactive liposome with an average particle size of 221 nm and a CV value of 18% was obtained.

EXAMPLE 3-8

The procedures of Example 3-1 were pursued with the exception that the yolk phosphatidylcholine was replaced by 1,2-di(2,4-octadecadienoyl)-glycero-3-phosphocholine (DODPC), whereby a reactive liposome as a large unilamellar vesicle with an average particle size of 254 nm (CV value 23%) which exhibited a polymerizability was obtained. By irradiating this liposome with a γ-ray of 0.75 Mrad, a polymerization of DODPC was attained. The polymerized liposome was subjected to gel filtration with Sephadex G-50 and then to freeze drying, whereby a powdery sample was obtained. This liposome powder was able to be regenerated by causing it to swell with physiological saline.

EXAMPLE 4-1

20 mg (26 μmol) of yolk phosphatidylcholine and 3.9 mg (10 μmol) of cholesterol were placed in an eggplant type flask together with 10% by weight, based on the above two compounds, (2.4 mg: 0.8 μmol) of a reactive phospholipid derivative obtained in Example 2-1 [a reactive phospholipid derivative of the general formula (1-3) in which both $R^1C(=O)$ and $R^2C(=O)$ are a palmitoyl group, $R^3$ denotes a hydrogen atom, M denotes a sodium atom, OA is an oxyethylene group and n represents a number of about 45] and the mixture was dissolved in 2 ml of benzene, whereupon the mixture was subjected to freeze drying. Then, 1 ml of physiological saline was added thereto and, by treatment by a bath-type ultrasonication and using a vortex mixer, a mixture of multilayer liposomes was obtained. This mixture was then processed by an extruder by passing it through a series of three polycarbonate membranes of 3.0 μm, 1.0 μm and 0.2 μm successively in this order, whereby a reactive liposome as a large unilamellar vesicle was obtained. By determining the particle size of the resulting reactive liposome with a laser scattering size distribution meter [NICOMP 370HPL (Trademark) of NICOMP], an average particle size of 221 nm (with CV value of 19%) was found.

EXAMPLE 4-2

The procedures of Example 4-1 were pursued with the exception that 5% by weight (1 μmol) of a reactive phospholipid derivative of the general formula (1-3) in which both $R^1C(=O)$ and $R^2C(=O)$ are a myristoyl group, $R^3$ denotes a hydrogen atom, M denotes a sodium atom, OA is an oxyethylene group and n is a number of about 10 and 5% by weight (0.4 μmol) of dimyristoyl-glycero-phospho polyethylene glycol (MW=ca. 2,000) were used in the place of the reactive phospholipid derivative of Example 2-1, whereby a reactive liposome was obtained (average particle size=268 nm, CV value=22%).

EXAMPLE 4-3

The procedures of Example 4-1 were pursued with the exception that 30% by weight (3.5 μmol) of a reactive phospholipid derivative of the general formula (1-3) in which both $R^1C(=O)$ and $R^2C(=O)$ are a myristoyl group, $R^3$ denotes a hydrogen atom, M denotes a sodium atom, OA is an oxyethylene group and n is a number of about 30 were used in the place of the reactive phospholipid derivative of Example 2-1, whereby a reactive liposome was obtained (average particle size=238 nm, CV value=22%).

EXAMPLE 4-4

The procedures of Example 4-1 were pursued with the exception that 1% by weight (0.1 μmol) of a reactive phospholipid derivative of the general formula (1-3), in which both $R^1C(=O)$ and $R^2C(=O)$ are a stearoyl group, $R^3$ denotes a hydrogen atom, M denotes a sodium atom and the oxyalkylene chain consists of a random addition polymeric chain composed of oxypropylene groups (average addition mole number=ca. 10) and oxyethylene groups (average addition mole number=ca. 25), and 5% by weight (0.4 μmol) of dimyristoyl-glycero-phospho polyethylene glycol (MW=ca. 2,000) were used in the place of the reactive phospholipid derivative of Example 2-1, whereby a reactive liposome was obtained (average particle size=239 nm, CV value=25%).

EXAMPLE 4-5

The procedures of Example 4-1 were pursued with the exception that 5% by weight (0.6 μmol) of a reactive phospholipid derivative of the general formula (1-3) in which both $R^1C(=O)$ and $R^2C(=O)$ are a stearoyl group, $R^3$ denotes a hydrogen atom, M denotes a sodium atom and the oxyalkylene chain consists of a block-addition polymeric chain composed of a polyoxypropylene block (average addition mole number=ca. 10) and a polyoxyethylene block (average addition mole number=ca. 15) were used in the place of the reactive phospholipid derivative of Example 2-1, whereby a reactive liposome was obtained (average particle size=247 nm, CV value=19%).

EXAMPLE 4-6

The procedures of Example 4-1 were pursued with the exception that 5% by weight (0.1 μmol) of a reactive phospholipid derivative of the general formula (1-3) in which both $R^1C(=O)$ and $R^2C(=O)$ are a stearoyl group, $R^3$ denotes a hydrogen atom, M denotes a sodium atom and the oxyalkylene chain consists of a block-addition polymeric chain composed of a polyoxytetramethylene block (average addition mole number=5) and a polyoxyethylene block (average addition mole number=ca. 278) were used in the place of the reactive phospholipid derivative of Example 2-1, whereby a reactive liposome was obtained (average particle size=290 nm, CV value=23%).

EXAMPLE 4-7

The procedures of Example 4-1 were pursued with the exception that 20% by weight (4.2 μmol) of a reactive phospholipid derivative of the general formula (1-3) in which both $R^1C(=O)$ and $R^2C(=O)$ are a myristoyl group, $R^3$ is methyl, M is sodium atom, OA is an oxyethylene group and n is a number of about 10 were used in the place of the reactive phospholipid derivative of Example 2-1, whereby a reactive liposome was obtained (average particle size=211 nm, CV value= 19%).

EXAMPLE 4-8

The procedures of Example 4-1 were pursued with the exception that the yolk phosphatidylcholine was replaced by 1,2-di(2,4-octadecadienoyl)-glycero-3-phosphocholine (DODPC), whereby a reactive liposome as a large unilamellar vesicle with an average particle size of 254 nm (CV value 23%) which exhibited a polymerizability was obtained. By irradiating this liposome with a γ-ray of 0.75 Mrad, a polymerization of DODPC was attained. The polymerized liposome was subjected to gel filtration with Sephadex G-50 and then to freeze drying, whereby a powdery sample was obtained. This liposome powder was able to be regenerated by causing it to swell with physiological saline.

EXAMPLE 5-1

0.5 ml of the reactive liposome solution (solid matter content 2.5% by weight) obtained in Example 3-1 was stirred together with a 0.1M phosphate buffer (pH 7.5) containing 1 mg/ml of horseradish-peroxidase (abbreviated as HRP) at 4° C. for 24 hours, whereby HRP was fixed onto the reactive liposome. This was processed by a gel filtration with Sephadex G-50 to collect the liposome-containing fraction. 0.1 ml of a solution (10 mmol/l) of 1,2-phenylenediamine which is a substrate for HRP is added to the so-collected fraction and the mixture was incubated at 30° C. for 10 minutes. By adding to this 10 μl of 0.1N sulfuric acid, a coloration into brown was observed.

By this, it was confirmed that HRP can be fixed on the reactive liposome of Example 3-1 simply by stirring together with it.

EXAMPLE 6-1

0.5 ml of the reactive liposome solution (solid matter content 2.5% by weight) obtained in Example 4-1 was stirred together with a 0.1M phosphate buffer (pH 7.5) containing 1 mg/ml of HRP at 4° C. for 24 hours, whereby HRP was fixed on the reactive liposome. This HRP-fixed liposome was processed by a gel filtration with Sephadex G-50 to collect the liposome-containing fraction. 0.1 ml of a solution (10 mmol/l) of 1,2-phenylenediamine which is a substrate for HRP is added to the so-collected fraction and the mixture was incubated at 30° C. for 10 minutes. By adding to this 10 μl of 0.1N sulfuric acid, a brown coloration was observed.

From this, it was confirmed that HRP can be fixed on the reactive liposome of Example 4-1 simply by stirring together.

Comparative Example 1

The procedures of Example 3-1 were followed under the use of only the yolk phosphatidylcholine and the cholestrol in amounts of 20 mg (26 μmol) and 3.9 mg (10 μmol) respectively, whereby a large monolayer liposome with 2.5 wt. % solid was obtained. When this liposome was processed by reacting HRP thereto, purifying by gel filtration, adding thereto 0.1 ml of a solution of 1,2-phenylenediamine and incubating the mixture at 30° C. for 10 minutes, followed by addition of 10 μl of 0.1N sulfuric acid, in the same manner as in Example 5-1, no coloration was found.

From this, it was shown that the liposome of this Comparative Example 1 without containing the reactive phospholipid derivative was not able to fix HRP thereon.

We claim:

1. A phospholipid derivative represented by the general formula (1):

$$\begin{array}{c} H_2C-OC-R^1 \\ \phantom{H_2C-O}\| \\ \phantom{H_2C-OC}O \\ R^2-CO-CH \phantom{xxx} O \phantom{xxxxxxxxxxxxxx} R^3 \\ \phantom{R}\| \phantom{xx}| \phantom{xxx}\| \phantom{xxxxxxxxxxxxxxx} \diagup= N \\ \phantom{R^2-C}O \phantom{x} H_2C-OP-(X)_p-(OA)_n-O-C-N \phantom{xxxx} | \\ \phantom{xxxxxxxxxxxxx}| \phantom{xxxxxxxxxxxxx} \| \phantom{xxx} \diagdown= \\ \phantom{xxxxxxxxxxxxx}OM \phantom{xxxxxxxxxxxxxx} O \end{array} \quad (1)$$

in which $R^1C(=O)$ and $R^2C(=O)$ represent each an aliphatic acyl group having 3–30 carbon atoms and may be identical or different from each other, $R^3$ denotes hydrogen atom or methyl group, OA represents an oxyalkylene group of 2–4 carbon atoms, n indicates the average addition mole number of added oxyalkylene group and is a positive number of 1–1,000, with the proviso that the oxyalkylene groups may be identical or different from each other and may be added randomly or in a block when n is 2 or higher, p is 0 or 1, X represents the group

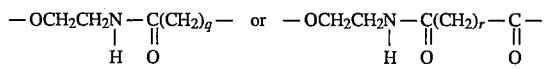

wherein q is an integer of 0 to 4 and r is an integer of 1 to 4 and

M denotes hydrogen atom or an alkali metal atom.

2. A phospholipid derivative as claimed in claim 1 represented by the general formula (1-1):

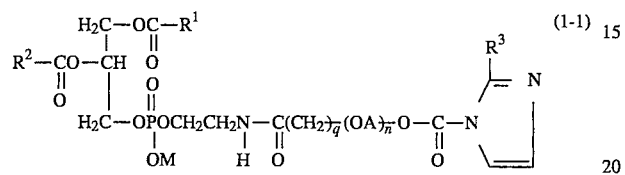

in which $R^1C(=O)$ and $R^2C(=O)$ represent each an aliphatic acyl group having 3–30 carbon atoms and may be identical or different from each other, $R^3$ denotes hydrogen atom or methyl group, OA represents an oxyalkylene group of 2–4 carbon atoms, n indicates the average addition mole number of added oxyalkylene group and is a positive number of 1–1,000, with the proviso that the oxyalkylene groups may be identical or different from each other and may be added randomly or in a block when n is 2 or higher, q is an integer of 0–4 and M denotes hydrogen atom or an alkali metal atom.

3. A phospholipid derivative as claimed in claim 1 represented by the general formula (1-2):

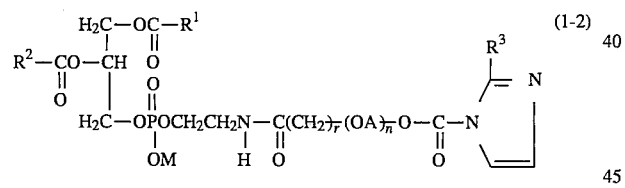

in which $R^1C(=O)$ and $R^2C(=O)$ represent each an aliphatic acyl group having 3–30 carbon atoms and may be identical or different from each other, $R^3$ denotes hydrogen atom or methyl group, OA represents an oxyalkylene group of 2–4 carbon atoms, n indicates the average addition mole number of added oxyalkylene group and is a positive number of 1–1,000, with the proviso that the oxyalkylene groups may be identical or different from each other and may be added randomly or in a block when n is 2 or higher, r is an integer of 1–4 and M denotes hydrogen atom or an alkali metal atom.

4. A phospholipid derivative as claimed in claim 1 represented by the general formula (1-3):

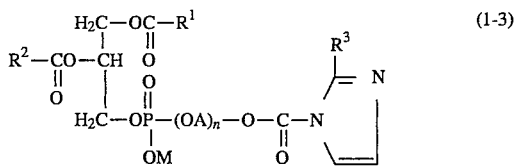

in which $R^1C(=O)$ and $R^2C(=O)$ represent each an aliphatic acyl group having 3–30 carbon atoms and may be identical or different from each other, $R^3$ denotes hydrogen atom or methyl group, OA represents an oxyalkylene group of 2–4 carbon atoms, n indicates the average addition mole number of added oxyalkylene group and is a positive number of 1–1,000, with the proviso that the oxyalkylene groups may be identical or different from each other and may be added randomly or in a block when n is 2 or higher and M denotes hydrogen atom or an alkali metal atom.

* * * * *

UNITED STATES PATENT AND TRADEMARK OFFICE
CERTIFICATE OF CORRECTION

PATENT NO. : 5,463,066
DATED : October 31, 1995
INVENTOR(S) : Tsuyoshi MIYAZAKI et al It is certified that error appears in the above-indentified patent and that said Letters Patent is hereby corrected as shown below:

Column 27, lines 39-45; correct the formula to read as follows:

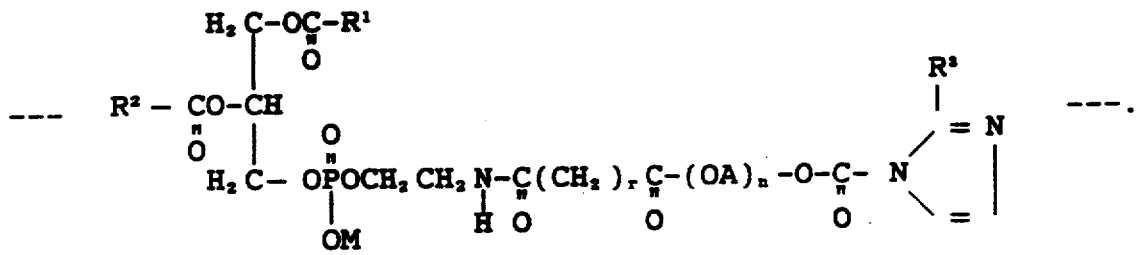

Signed and Sealed this

Eleventh Day of June, 1996

Attest:

BRUCE LEHMAN

Attesting Officer

Commissioner of Patents and Trademarks